(12) United States Patent
Woehr

(10) Patent No.: US 9,399,098 B2
(45) Date of Patent: Jul. 26, 2016

(54) FLUSHING MEDICAL DEVICES

(75) Inventor: Kevin Woehr, Felsberg (DE)

(73) Assignee: B. Braun Melsungen AG, Melsungen (DE)

( * ) Notice: Subject to any disclaimer, the term of this patent is extended or adjusted under 35 U.S.C. 154(b) by 4 days.

(21) Appl. No.: 13/984,188

(22) PCT Filed: Feb. 23, 2012

(86) PCT No.: PCT/EP2012/053070
§ 371 (c)(1),
(2), (4) Date: Aug. 22, 2013

(87) PCT Pub. No.: WO2012/113865
PCT Pub. Date: Aug. 30, 2012

(65) Prior Publication Data
US 2013/0331817 A1    Dec. 12, 2013

Related U.S. Application Data

(60) Provisional application No. 61/446,821, filed on Feb. 25, 2011.

(51) Int. Cl.
*A61M 5/31* (2006.01)
*A61M 5/34* (2006.01)
*A61M 39/10* (2006.01)

(52) U.S. Cl.
CPC ............. *A61M 5/31* (2013.01); *A61M 5/3134* (2013.01); *A61M 5/347* (2013.01); *A61M 2039/1033* (2013.01); *A61M 2039/1077* (2013.01); *A61M 2206/10* (2013.01)

(58) Field of Classification Search
CPC .................. A61M 5/3134; A61M 2005/3132; A61M 5/347; A61M 2039/1077; A61M 2039/1033; A61M 2206/10; A61M 2039/0018; A61M 39/225; A61M 2005/1787; A61M 5/31
USPC .................................................. 604/239, 241
See application file for complete search history.

(56) References Cited

U.S. PATENT DOCUMENTS

| 4,267,835 A | * | 5/1981 | Barger ................ A61M 39/225 |
| | | | 251/117 |
| 5,533,983 A | * | 7/1996 | Haining ........................ 604/249 |

(Continued)

FOREIGN PATENT DOCUMENTS

| EP | 0 544655 B1 | 10/1995 |
| WO | WO 2006/062912 A1 | 6/2006 |
| WO | WO 2010/109449 A1 | 9/2010 |

OTHER PUBLICATIONS

International Search Report mailed Jun. 15, 2012 from corresponding International Application No. PCT/EP2012/053070 filed Feb. 23, 2012 (6 pages).

(Continued)

*Primary Examiner* — Theodore Stigell
(74) *Attorney, Agent, or Firm* — Klein, O'Neill & Singh, LLP

(57) ABSTRACT

Syringes and flushing medical devices are generally discussed herein for withdrawing, injecting, or instilling fluids. More particularly, syringe tips and flushing tip adaptors with multiple flow channels are discussed for flushing vascular access devices. The tips have cut-outs that are located and sized to produce a relatively wider flow profile than a typical syringe tip with a single central lumen to facilitate flushing the vascular access devices.

21 Claims, 13 Drawing Sheets

(56) References Cited

U.S. PATENT DOCUMENTS

| | | |
|---|---|---|
| 5,651,776 A | 7/1997 | Appling et al. |
| 5,947,954 A | 9/1999 | Bonaldo |
| 6,830,563 B1 | 12/2004 | Singer |
| 2006/0129109 A1* | 6/2006 | Shaw et al. ............... 604/246 |
| 2009/0143770 A1* | 6/2009 | Robinson ............. A61M 39/10 604/533 |
| 2010/0204648 A1* | 8/2010 | Stout et al. ............... 604/122 |
| 2010/0204660 A1 | 8/2010 | McKinnon et al. |

OTHER PUBLICATIONS

Written Opinion mailed Jun. 15, 2012 from corresponding International Application No. PCT/EP2012/053070 filed Feb. 23, 2012 (8 pages).

Examiner's Report on corresponding foreign application (CN Application No. 201280010296.4) from the State Intellectual Property Office dated May 9, 2016.

* cited by examiner

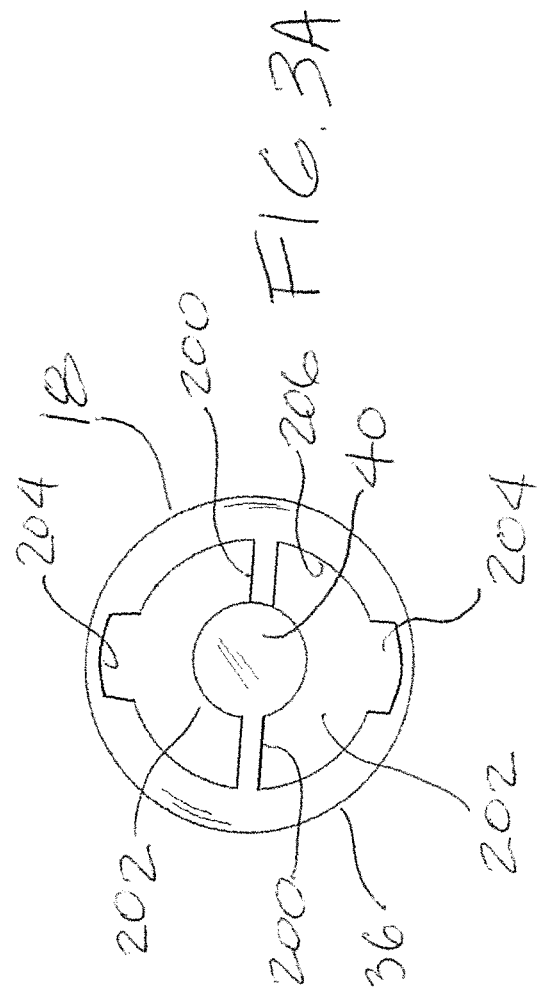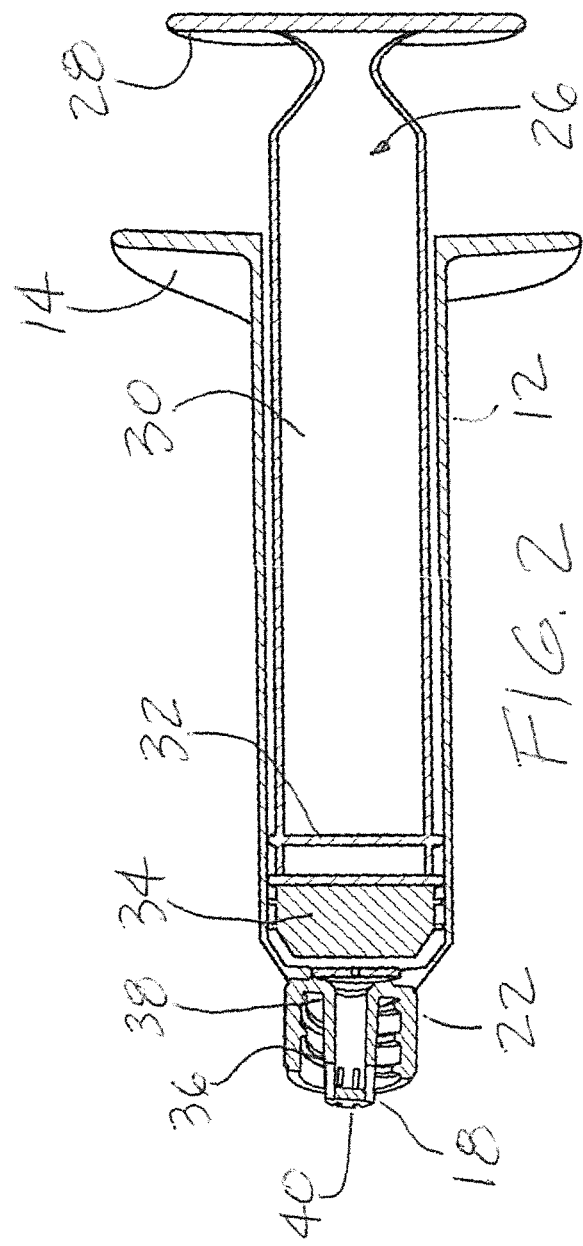

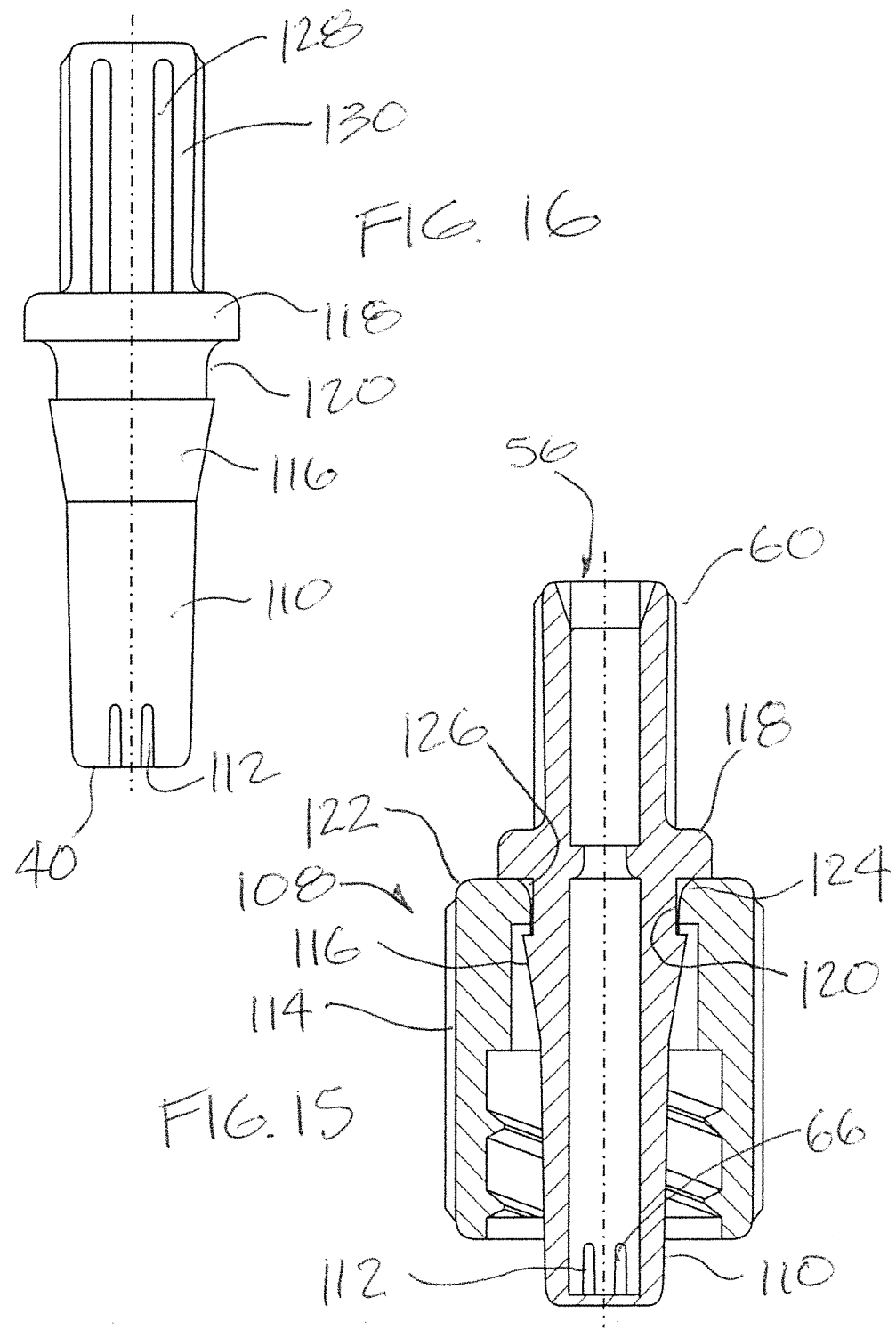

FLUSHING MEDICAL DEVICES

Syringes and flushing medical devices are generally discussed herein for withdrawing, injecting, or instilling fluids. More particularly, syringe tips and flushing tip adaptors with multiple flow channels are discussed for flushing vascular access devices.

BACKGROUND

A prior art syringe typically has a barrel with a syringe tip and a plunger. A single lumen is usually formed through the syringe tip. When fluid discharges out the syringe tip, the single lumen produces a single stream of predictable close or tight pattern.

The syringe tip is typically made with a certain industry wide standard taper or Luer taper. The taper allows different syringe tips produced from different manufacturers to match or mate with medical devices having companion female Luer tapers.

SUMMARY

The various embodiments of the present flushing medical devices and related methods have several features, no single one of which is solely responsible for their desirable attributes. Without limiting the scope of the present embodiments as expressed by the claims that follow, their more prominent features now will be discussed briefly. After considering this discussion, and particularly after reading the section entitled "Detailed Description," one will understand how the features of the present embodiments provide advantages, which include the capability of providing a wide flow pattern for flushing vascular access devices.

A flushing medical device comprising a tip for flushing a vascular access device, such as a needleless access port valve, a catheter, and a male Luer connector, is provided. In one example, a tip having body is provided comprising a tip end that is generally orthogonal to a side wall having a Luer taper and wherein the tip end and the side wall define an intersection therebetween. In one example, the side wall has a greater surface area than a surface area on the tip end. The device further includes a lumen formed by the side wall and wherein two or more spaced-apart cut-outs are formed through the side wall and through at least part of the intersection. In another example, only one cut-out is formed through the side wall and through at least part of the intersection.

Further in accordance with the present device, a receiving end located opposite the tip end is provided, the receiving end having an interior wall surface with a female Luer taper.

The flushing medical device can further include a tapered skirt section and a flange defining a notch therebetween and on the body. A collar may be located at the notch. The collar can be rotatable relative to the body. The flushing medical device, however, can be practiced without the collar.

The flushing medical device with the flushing tip can be part of a syringe and attached to a syringe barrel and having a plunger having a push flange slidably disposed therein. The syringe barrel can have different volumetric sizes.

To cover the tip, such as during packaging and/or shipping, a cap can be fitted over the tip. The cap can also threadedly engage the threaded collar.

The flushing medical device can further include cut-outs formed on the surface area of the tip end. The cut-outs can have various shapes, such as a trapezoidal shape, a generally rectangular shape, a square shape, a spiral shape, and slanted shape.

The flushing medical device can optionally include a perimeter defining an opening formed only on the surface area of the tip end. The opening can function as an additional flow port or channel or for use to accommodate a spike of a needleless access port valve.

Another flushing medical device example is one that includes a tip having a body comprising a tip end that is generally orthogonal to a side wall having a Luer taper, wherein the tip end and the side wall define an intersection therebetween and wherein the side wall has a greater surface area than a surface area on the tip end. A lumen is formed by the side wall and a receiving end having a female Luer taper is disposed at an end opposite the tip end. A threaded collar can be located exteriorly of the body and wherein two or more spaced-apart cut-outs are formed through the side wall and through at least part of the intersection. In another example, only a single flow channel is formed through the sidewall.

Yet another flushing medical device example is one that includes a tip having a body comprising a tip end that is generally orthogonal to a side wall having a Luer taper, wherein the tip end and the side wall define an intersection therebetween and wherein the side wall has a greater surface area than a surface area on the tip end. A lumen is formed by the side wall and a barrel is attached to the tip. A plunger is slidably disposed inside the barrel and wherein two or more spaced-apart cut-outs are formed through the side wall and through at least part of the intersection.

The present application further includes a method for flushing a vascular access device. The method comprising pressing a plunger into a syringe barrel or pumping by means of an automated infusion device; discharging a single flow stream into a flushing medical device; and discharging multiple streams out of multiple flow channels at a tip of the flushing medical device. In another example, a flow stream is discharged out a single flow channel and wherein the single flow channel is formed as a cut-out through the side wall of the tip.

BRIEF DESCRIPTION OF THE DRAWINGS

The various embodiments of the present apparatus, systems, and associated methods now will be discussed in detail with an emphasis on highlighting the advantageous features. These embodiments depict the novel and non-obvious apparatus shown in the accompanying drawings, which are for illustrative purposes only. These drawings include the following figures, in which like numerals indicate like parts:

FIG. 2 is a side cross-sectional, partial perspective, view of the syringe of FIG. 1;

FIG. 3A is a front view of a syringe tip provided in accordance with an alternative example;

FIG. 15 is a cross-sectional side view of an alternative flushing tip adaptor having a rotatable threaded collar provided in accordance with the aspects of the present device, system, and method;

FIG. 16 is a side view of the flushing tip adaptor of FIG. 15 shown without the rotatable threaded collar;

DETAILED DESCRIPTION

The detailed description set forth below in connection with the appended drawings is intended as a description of the presently preferred embodiments of flushing medical devices, such as syringes and flushing tip adaptors, provided in accordance with aspects of the present device, system, and method and are not intended to represent the only forms in which the present device, system, and method may be constructed or utilized. The description sets forth the features and the steps for constructing and using the flushing medical devices of the present device, system, and method in connection with the illustrated embodiments. It is to be understood, however, that the same or equivalent functions and structures may be accomplished by different embodiments that are also intended to be encompassed within the spirit and scope of the present device, system, and method. As denoted elsewhere herein, like element numbers are intended to indicate like or similar elements.

As discussed herein, the word "proximal" is intended to designate an end of a device closer to the user than to the patient, when in normal use. The word "distal" is intended to designate an end the device closer to the patient than to the user. Unless the context indicates otherwise, the words "proximal" and "distal" do not require most proximal end point or most distal end point, although such end points fall within the scope of the respective words.

Figure 1:
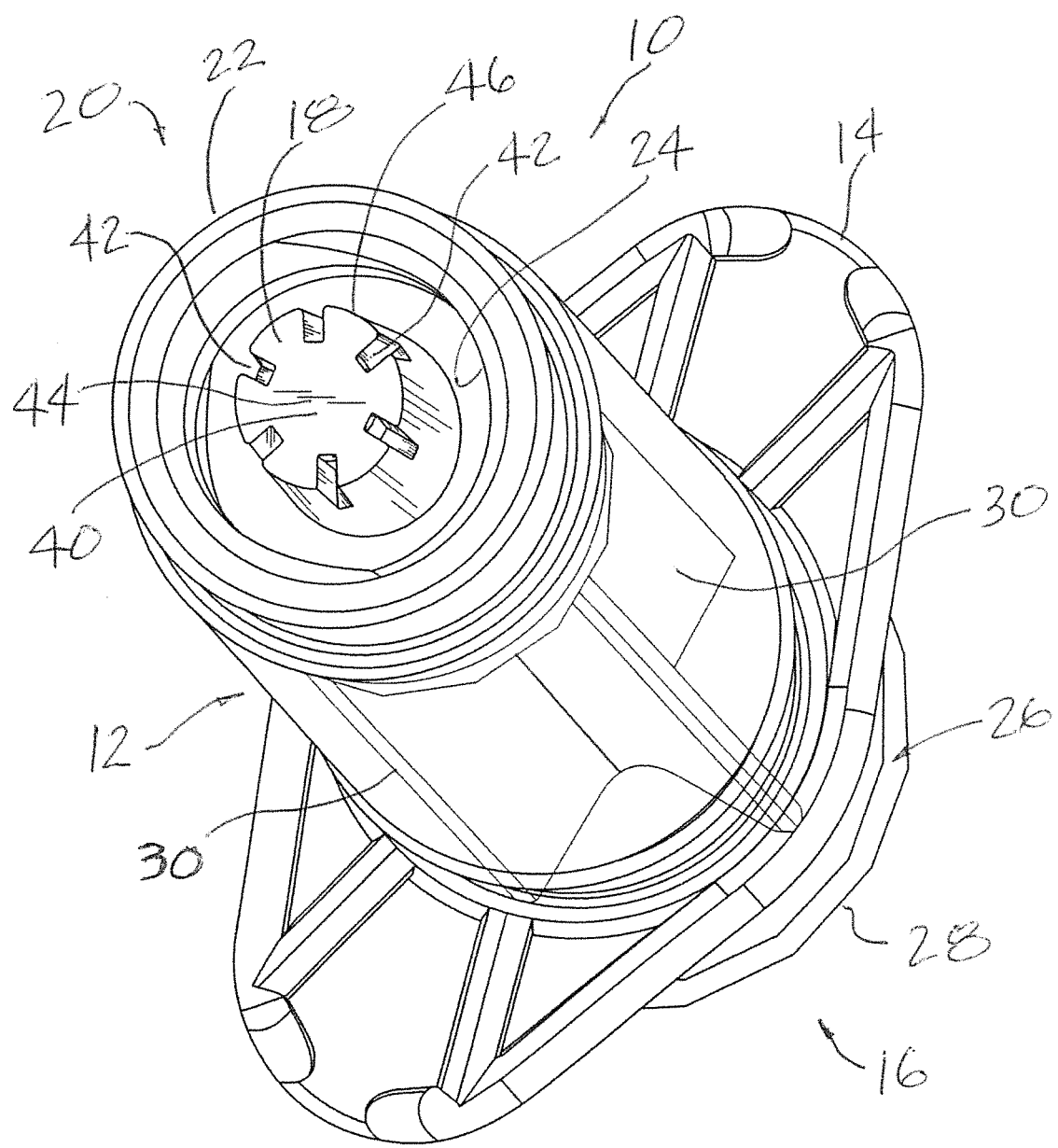
FIG. 1 shows a perspective view of a syringe having a syringe tip with multiple flow channels.

FIG. 1 shows a perspective view of a syringe 10 provided in accordance with aspects of the present device, system, and method. In one embodiment, the syringe 10 comprises a barrel 12 having a gripping flange 14 at a proximal end 16 and a syringe tip 18 at a distal end 20, which is preferably a Luer tip for mating engagement with a female Luer, such as a catheter hub, a needleless port access valve, a male Luer connector, and the like. Exemplary needleless port access valves are disclosed in U.S. Pat. Nos. 5,439,451 and 5,700,248, which are expressly incorporated herein by reference for all purposes. Exemplary male Luer connectors are disclosed in U.S. Pat. Nos. 6,964,406 and 7,803,140, the contents of which are expressly incorporated herein by reference for all purposes. Exemplary catheter assemblies are disclosed in U.S. Pat. Nos. 7,736,339; 7,374,554; 7,625,360; 5,879,337; and 6,629,959 and in publication No. WO 2010/093792 A1, filed Feb. 11, 2010; the contents of which are expressly incorporated herein by reference for all purposes.

As shown, the syringe 10 includes a collar 22 with internal threads 24 for use as a Luer lock. However, the syringe 10 may be practiced without the threaded collar, for use as a Luer slip. A piston or plunger 26 have a plunger tip 34 (FIG. 2) and a push flange 28 is slidably positioned inside the syringe barrel for aspirating or expelling fluids from the barrel. In one example, the plunger 26 is made from a plurality of longitudinal ribs 30 and radial ribs 32 (FIG. 2). In another example, the plunger is made from a central core or rod with one or more ribs and without a plunger tip. In other words, the plunger stem and plunger tip are integrally formed and is commonly referred to as a two-piece syringe in the industry. The syringe of FIG. 2 is commonly referred to as a three-piece syringe in the industry.

The syringe 10 may be made from a number of known prior art plastic materials using known methods. The syringe 10 is preferably made from a transparent or semi-transparent material to permit viewing through the syringe barrel. Less preferred, the syringe barrel is made from an opaque material. Graduated marks, scale, logo, and/or other indicia, such as lot number, may be printed on the outside of the syringe barrel for reference purposes.

With reference to FIG. 2 in addition to FIG. 1, the syringe tip 18 comprises an elongated body 36 comprising a base 38 connected to the distal end of the syringe barrel and a tip end 40 having a generally planar end surface, which may be practiced with an arc or taper. In the example shown, a central section 44 of the tip end 40 is solid and does not incorporate a lumen. Instead, multiple flow channels 42 are incorporated radially of the central portion 44. In one example, the flow channels 42 are each generally rectangular or rectilinear in shape and includes at least a cut-out formed on or through the tip end 40. More preferably, each flow channel 42 is formed by a cut-out formed through both the tip end 40 and the tip body 36, at the intersection thereof. Although six flow channels 42 are shown, fewer or more than six flow channels may be incorporated.

In one specific example, each flow channel 42 is formed at or through the intersection 46 of the tip end 40 and the tip body 36 so that when fluid is expelled through the syringe tip, fluid flows axially, radially, both axially and radially, and/or randomly. However, each flow channel 42 may be formed by providing a cut-out through the tip end only and not the tip body so that when fluid is expelled through the syringe tip, fluid flows axially only through the plurality of axial cut-outs. One or more protrusions or projections (not shown) may be incorporated at the tip end 40 for the axial only flow embodiment to avoid sealing or obstructing the flow channels 42, such as when the tip end abuts a flat surface that can potentially seal the axial only flow channels. As further discussed below, fluid discharging through the tip of the present syringe has a generally large flow pattern compared to the flow pattern of a prior art syringe having a single central lumen.

Figure 3:
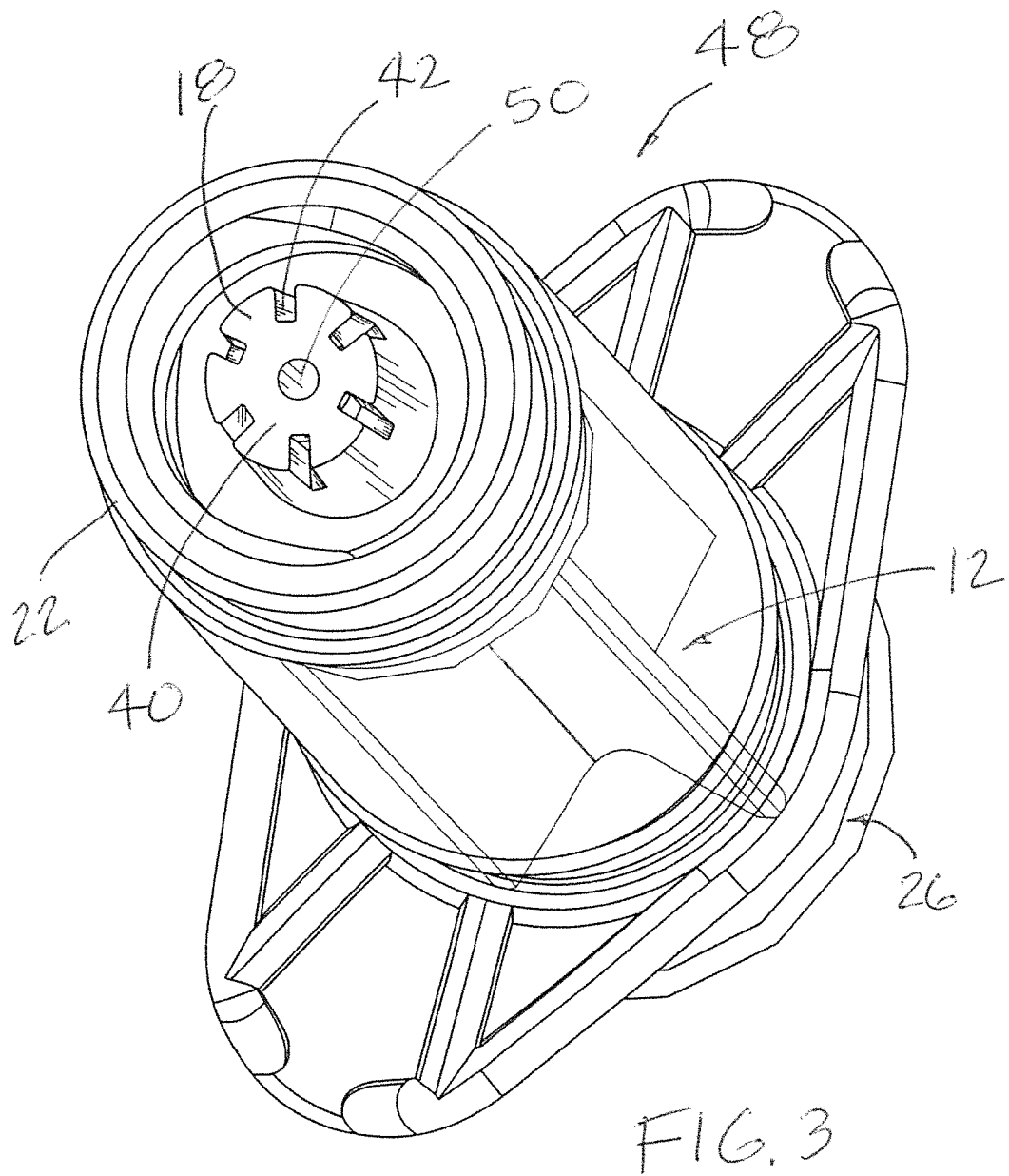
FIG. 3 is a perspective view of an alternative syringe having a syringe tip with multiple flow channels and a central flow port.

Refer now to FIG. 3, a perspective view of an alternative syringe 48 is shown having a syringe tip 18 with multiple flow channels 42 and a generally centrally located port 50. The centrally located port 50 may have a circular shape and may vary in diameter relative to the radially located flow channels 42. For example, if more fluid flow is intended to flow through the radially located flow channels 42, then the central port 50 may have a relatively smaller diameter than when less fluid flow is intended to flow through the radially located flow channels 42. In other embodiments, the centrally located flow port 50 has a non-circular shape or configuration, such as rectangular, oval, triangular, irregular, etc., and may be located off-center on the tip end 40. Additionally, one or more protrusions may be incorporated at the tip end to prevent sealing the central port 50 and the flow channels 42 against a generally planar surface.

In yet another embodiment, the central port 50 is sized to accommodate a spike located inside a seal of a needless access port valve, such as those shown in U.S. Pat. No. 5,700, 248. When inserted into the Luer inlet of a needleless access port valve of the '248 patent, the tip 18 of the syringe pushes down on the seal of the needleless access port valve to open the seal while the central port 50 surrounds the spike to accommodate its presence. Fluid flow discharging from the syringe would then flow through the various radially located flow channels 42 in flow pattern that is larger than a typical syringe to flush the interior surfaces of the needleless access port device.

The syringe of FIGS. 1-3 may be used by inserting the tip of the syringe into a vascular access device, such as into a female Luer connector of a catheter hub or a needleless access port valve, and, if the syringe has a threaded collar, rotating the syringe barrel to engage the collar with the threads on the vascular access device. The plunger on the syringe is then pushed to expel fluid out of the syringe tip. As the tip of the present syringe has multiple channels compared to a single lumen on a prior art syringe tip, fluid is expelled radially, axially, and/or randomly through the vascular access device to flush most, if not all, crevices of the internal chamber of the vascular access device. The flow channels of the disclosed syringes may also incorporate different shapes or configurations than shown, as further discussed below with reference to the various flushing tip adaptors.

FIG. 3A is a front view of an alternative syringe tip 18 provided in accordance with aspects of the present device. The syringe tip comprises a tip body 36 having a thickness and a tip end 40 connected to the tip body 36 by a pair of ribs or bridges 200. The tip end 40 and the bridges 200 define or form two opening passages 202 at the end of the tip. Fluid discharged through the tip 18 is configured to flow through the two passages 202 to produce a flow pattern. To increase surface area of the two opening passages 202, one or more optional undercuts 204 may be formed on the interior surface 206 of the tip body 36. The syringe tip 18 of the present embodiment can therefore provide a larger flow profile or pattern than a comparable single lumen prior art syringe.

Figure 4:
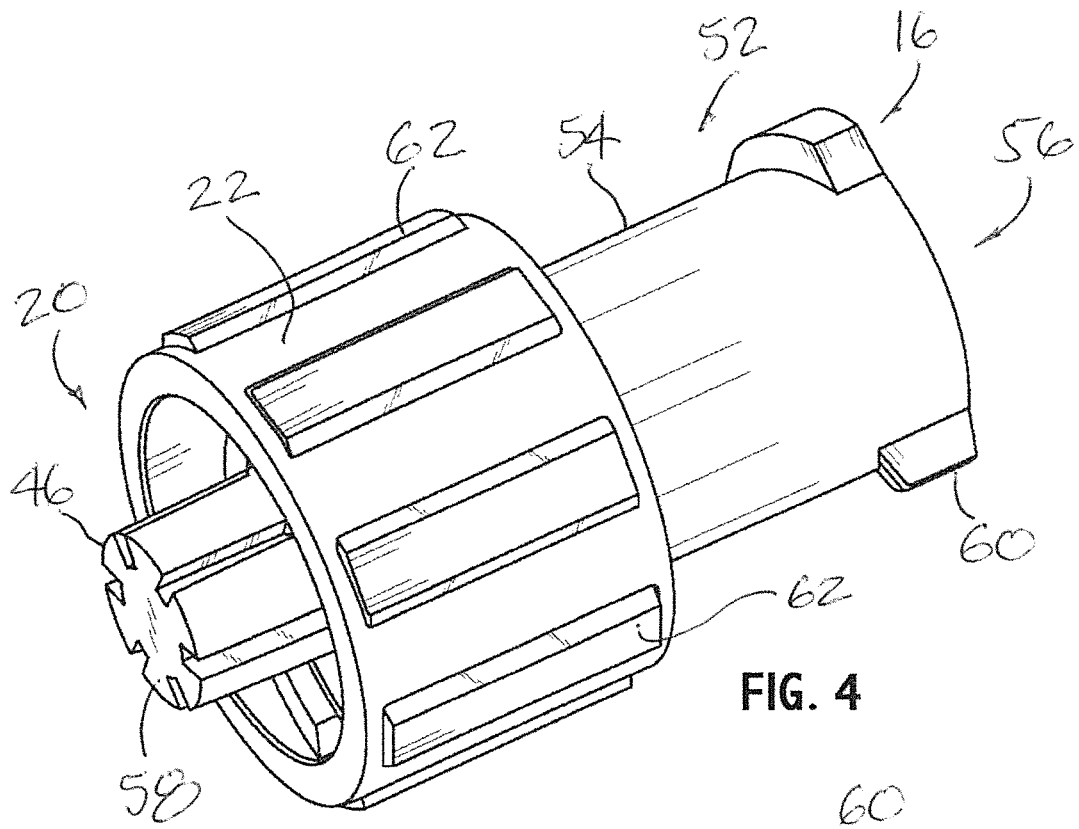
FIG. 4 shows a perspective view of a flushing tip adaptor provided in accordance with the aspects of the present device, system, and method.

FIG. 4 shows a perspective view of a flushing tip adaptor 52 provided in accordance with the aspects of the present device, system, and method. As shown, the flushing tip adaptor 52 comprises a body 54 having a receiving end 56, a proximal end 16, a tip 58 at a distal end 20, and a threaded collar 22 having internal threads located between the tip and the receiving end. The tip is preferably formed with a Luer taper for engaging a female Luer. A plurality of spaced apart projections 62 may be incorporated at the exterior surface of the threaded collar 22 to facilitate gripping the flushing tip adaptor. Preferably, the projections are equally spaced along the exterior surface. Alternatively, round or semi-spherical projections, such as bumps, are incorporated instead of elongated projections. The bumps may be randomly formed on the exterior surface or in an array. As shown, external threads 60 are incorporated at the proximal end 16 to provide a female Luer lock, as further discussed below.

Figure 5:
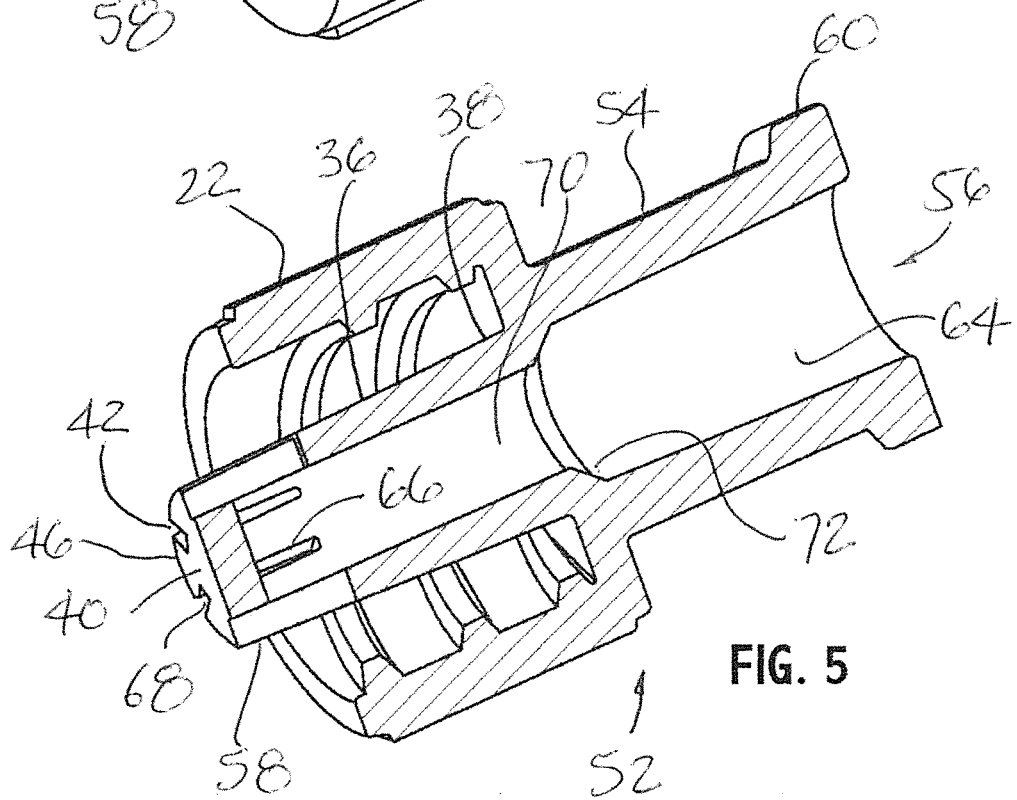
FIG. 5 is a side cross-sectional, partial perspective, view of the flushing tip adaptor of FIG. 4.

With reference to FIG. 5 in addition to FIG. 4, the receiving end 56 comprises a female Luer taper 64 and is configured to engage a male implement, such as a syringe tip. The receiving end 56 extends axially and reduces to a smaller nozzle 70 by a reducer or neck section 72. The smaller port is formed externally with a male Luer taper. If the male implement (not shown) has a threaded collar, it may engage the exterior threads 60 and threadedly lock to the proximal end of the flushing tip adaptor. The tip 58 and the collar 22 are shown singularly fabricated to the receiving end 56. However, the collar may be eliminated altogether or separately formed and subsequently attached to the body 54, as further discussed below.

The tip 58 is similar to the tip 18 shown in FIG. 1 and comprises a tip body 36, a tip base 38, a tip end 40, an intersection 46 between the tip end and the tip body, and a plurality of flow channels 42. As clearly shown, the flow channels 42 each include an axial cut-out section 66 and a radial cut-out section 68 and a planar tip end 40 that is generally solid, i.e., without a central lumen.

The flushing tip adaptor 58 is configured for use with a standard syringe having a standard Luer tip, either with or without a threaded collar. For example, the syringe tip (not shown) may be inserted into the receiving end 56 and held secured thereto by the Luer taper, or optionally with the threaded collar engaging the exterior threads 60. Once connected, the combination standard syringe (not shown) and flushing tip adaptor 58 is configured to perform the same or similar flushing function as discussed above for the FIGS. 1-3 syringes. More particularly, the flushing tip adaptor is configured to convert a single axial flow from a lumen of a standard syringe tip and diverting the flow into a plurality of flow streams that include axial, radial, both axial and radial, and/or random flow streams. The flow streams also collectively produce a flow pattern that is larger than the flow pattern of a typical prior art syringe having a single central lumen. In particular, the typical prior art syringe has a central opening and has a tendency to create a dead corner between the very distal end of the male Luer tip and the side wall of the female Luer taper. The present device is configure to eliminate this dead corner and directs flushing flow directly at the surfaces to reach this dead corner.

As shown in FIGS. 4 and 5 and as described, the flushing tip adaptor 58 is understood to include a body having a receiving end formed with a female Luer connector having a first interior diameter and a nozzle having a second inside diameter smaller than the first diameter with a plurality of flow channels formed at the distal end of the nozzle for diverting a single flow stream to multiple streams when exiting the nozzle. In one embodiment, the multiple streams include axial flow streams, radial flow streams, both axial and radial flow streams, and/or random streams. Thus, when used with a vascular access device, the multi-direction streams flow through most if not all of the sections or crevices of the vascular access device to flush the device. In a specific example, fluid flow out the Luer tip include streams that flow radially outwardly of the intersection 46 of the syringe tip. In comparison to a standard male Luer tip, the instant flushing tip adaptor 52 is configured to produce a wider spray or flow pattern than a single flow stream out a central lumen.

Figure 6:
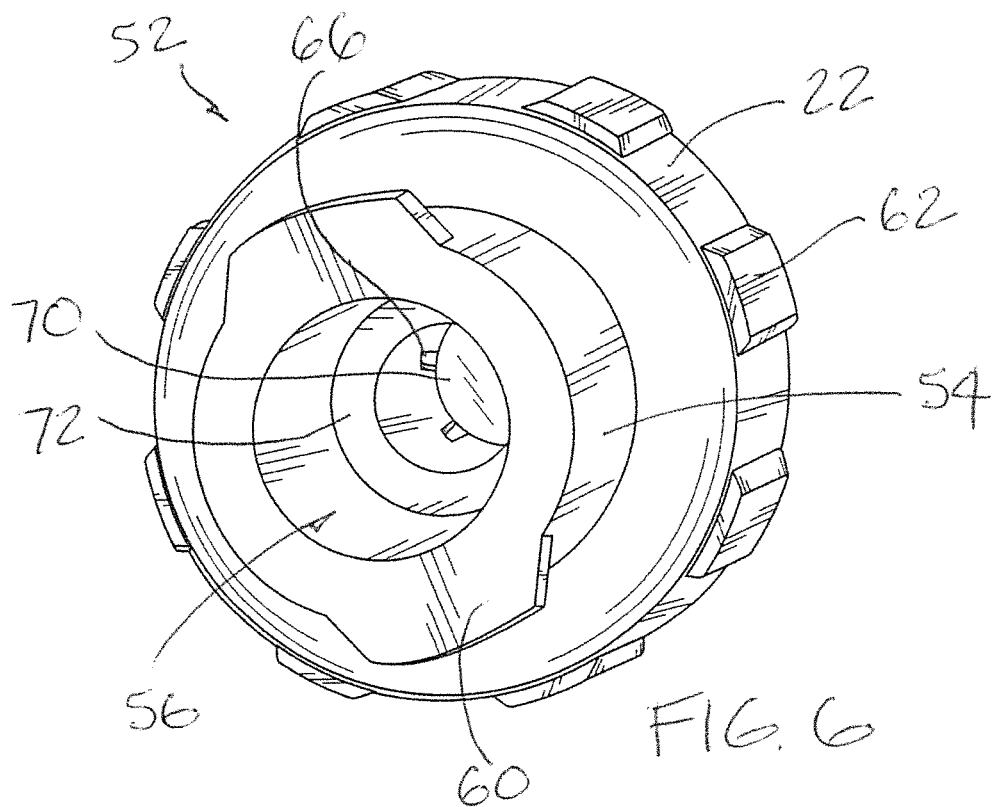
FIG. 6 is a perspective view of the flushing tip adaptor of FIG. 4 from a rear angle.

FIG. 6 is a perspective view of the flushing tip adaptor 52 of FIG. 4 viewed from a rear angle.

Figure 7:
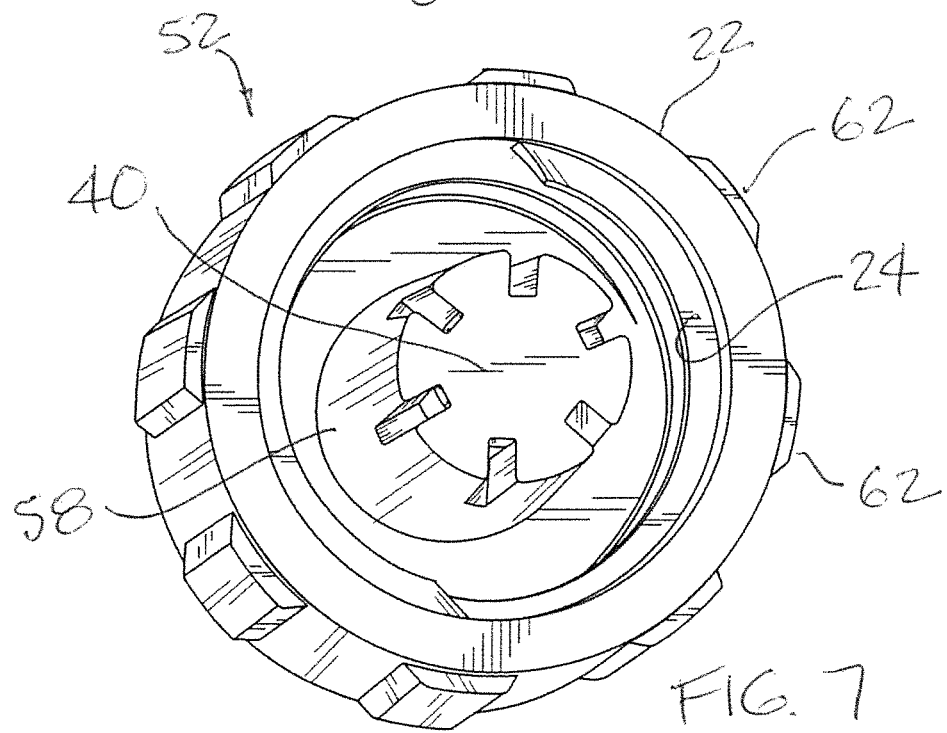
FIG. 7 is a perspective view of the flushing tip adaptor of FIG. 4 from another angle.

FIG. 7 is a perspective view of the flushing tip adaptor 52 of FIG. 4 viewed from another angle and looking at the tip. The flushing tip adaptor 52 may be made from a number of prior art plastic materials, such as PP, HDPE, PC, ABS, etc. The walls of the flushing tip adaptor may be opaque, semi-opaque, or transparent.

Figure 8:
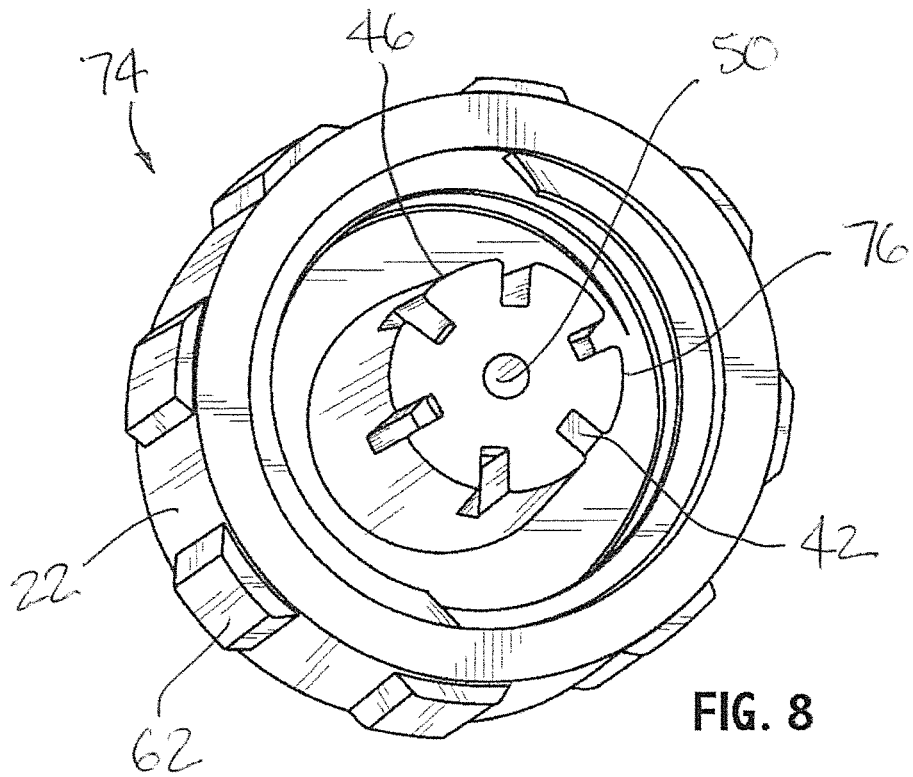
FIG. 8 is a perspective view of an alternative flushing tip adaptor having multiple flow channels and a central flow port.

FIG. 8 is a perspective view of an alternative flushing tip adaptor 72 having a tip 74 with multiple flow channels 42 and a central flow port 50. The tip 74 is similar to the tip of FIG. 3 in that it has both a central flow port 50 and radially located flow channels 42.

Figure 9:
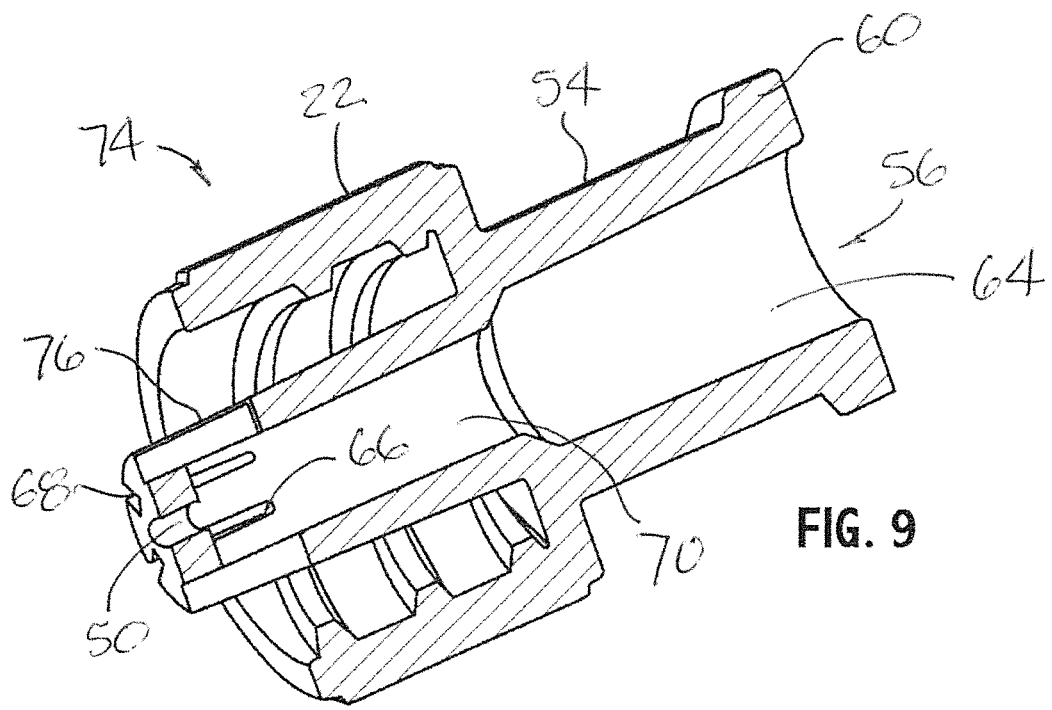
FIG. 9 is a side cross-sectional, partial perspective, view of the flushing tip adaptor of FIG. 8.

FIG. 9 is a side cross-sectional, partial perspective, view of the flushing tip adaptor 72 of FIG. 8. Axial cut-out sections 66 and radial cut-out sections of the flow channels 42 are clearly shown along with part of the central flow port 50.

Figure 10:
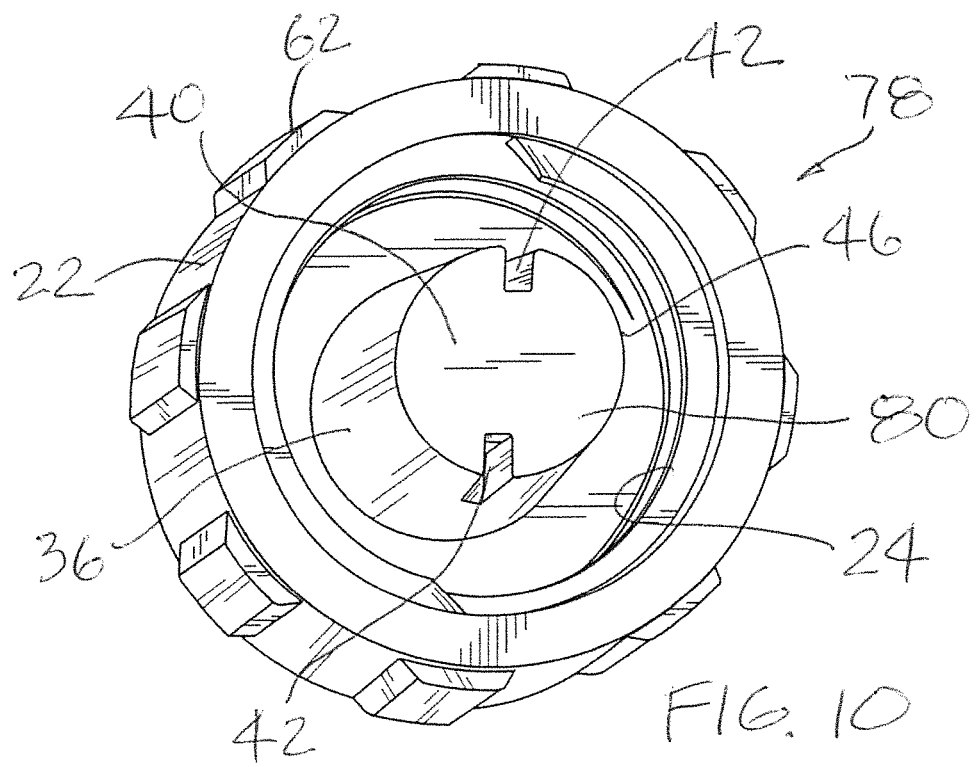
FIG. 10 is a perspective view of another alternative flushing tip adaptor having multiple flow channels.

FIG. 10 is a perspective view of another alternative flushing tip adaptor 78 having a tip 80 with two flow channels 42 formed through the tip end 40 and the tip body 36, and in particular through the intersection 46. The two flow channels 42 may be equally spaced apart along the perimeter of the tip at the intersection 46. However, more than two flow channels or a single flow channel may be incorporated without deviating from the present device. Although not shown, a central port 50 may be incorporated. By incorporating the instant flow channels at the tip, the adaptor is configured to produce a wider spray or flow pattern than a single flow stream out a central lumen of a typical prior art syringe.

Figure 11:
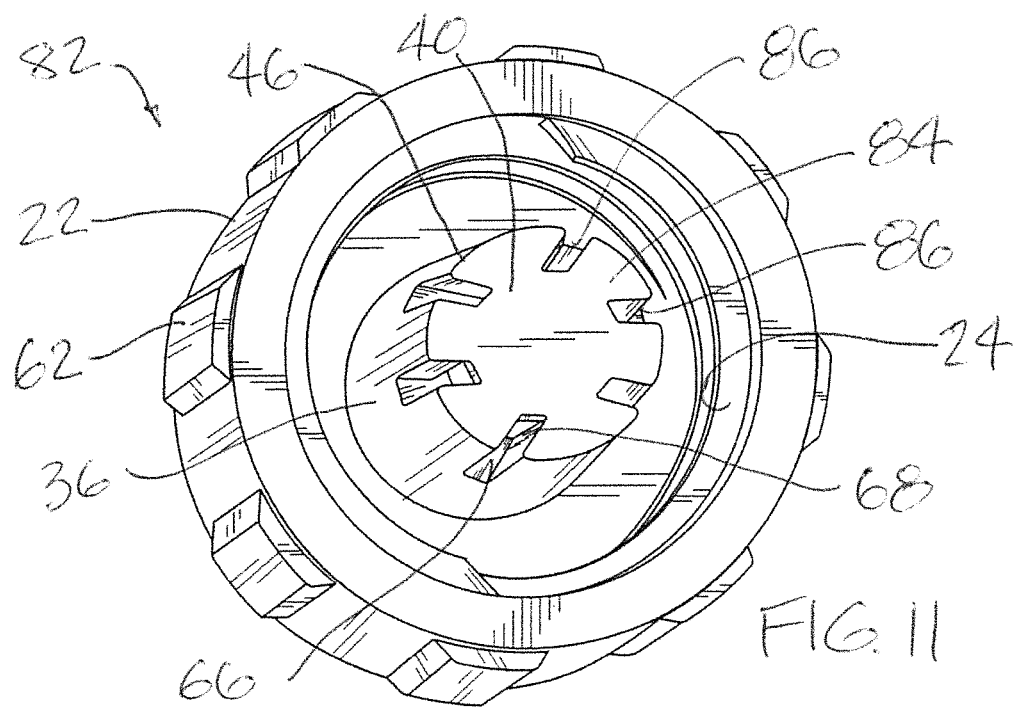
FIG. 11 is a perspective view of yet another alternative flushing tip adaptor having multiple flow channels.

FIG. 11 is a perspective view of yet another alternative flushing tip adaptor 82 having a tip 84 with multiple flow channels 86 and a threaded collar 22, which may optionally be omitted. The tip preferably has a body 36 formed with a Luer taper and the flow channels 86 each includes an axial cut-out and a radial cut-out. However, unlike the flow channels of, for example, FIGS. 3 and 8, the cut-outs are slanted relative to a central axis of the flushing tip adaptor 82, which is generally in the direction between the proximal and distal ends. For example, each axial cut-out 66 has two side walls that are generally parallel to one another but are angled relative to the central axis of the flushing tip adaptor 82. The bottom wall, located between the two side walls, may be perpendicular to the side walls or angled relative thereto. In other examples, the two side walls are not parallel to one another, as further discussed below. Although six flow channels 86 are shown, fewer or more than six flow channels may be incorporated. Also, a central port 50 may be incorporated.

In one example, each flow channel 86 has a radial cut-out 68 with two side walls that are generally parallel to one another and point generally to a central point on the tip end 40. In another example, the side walls point tangentially to the central point on the tip end 40 so that the multiple radial cut-outs are all slanted. In still other examples, the cut-outs are randomly formed along the intersection 46 with both radial and axial cut-outs. Less preferably, the cut-outs are randomly formed near the intersection 46 of the tip with only radial cut-outs 68. By incorporating the instant flow channels at the tip, the adaptor is configured to produce a wider spray or flow pattern than a single flow stream out a central lumen of a typical prior art syringe.

Figure 12:
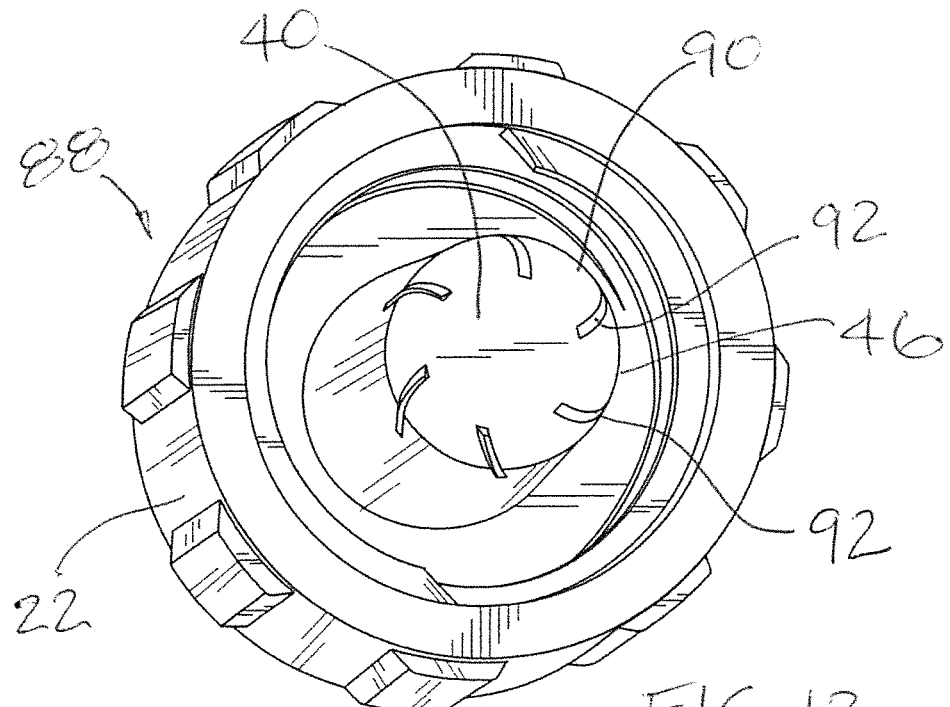
FIG. 12 is a perspective view of still yet another alternative flushing tip adaptor having multiple flow channels.

FIG. 12 is a perspective view of still yet another alternative flushing tip adaptor 88 having a tip 90 with multiple flow channels 92 and a threaded collar 22, which may optionally be omitted. In the present embodiment, the flow channels 92, while including radial cut-outs and axial cut-outs formed at the intersection 46, are formed with smooth spiral curves, which may be slanted clock-wise or counter-clockwise when viewing the tip 90 from a side view. Although six flow channels 92 are shown, fewer or more than six flow channels may be incorporated. Also, a central port 50 may be incorporated. By incorporating the instant flow channels at the tip, the adaptor is configured to produce a wider spray or flow pattern than a single flow stream out a central lumen of a typical prior art syringe.

In one example, a method is provided for manufacturing the flushing tip adaptor comprising injection molding a body having a tip and a collar. Forming a plurality of flow channels 92 having spiral curves that are slanted in a same clockwise or counter-clockwise direction as threads located on the collar 22. Ejecting the flushing tip adaptor from an injection pin using a same unscrewing direction for the slanted spiral curves and the threads on the collar.

Figure 13:
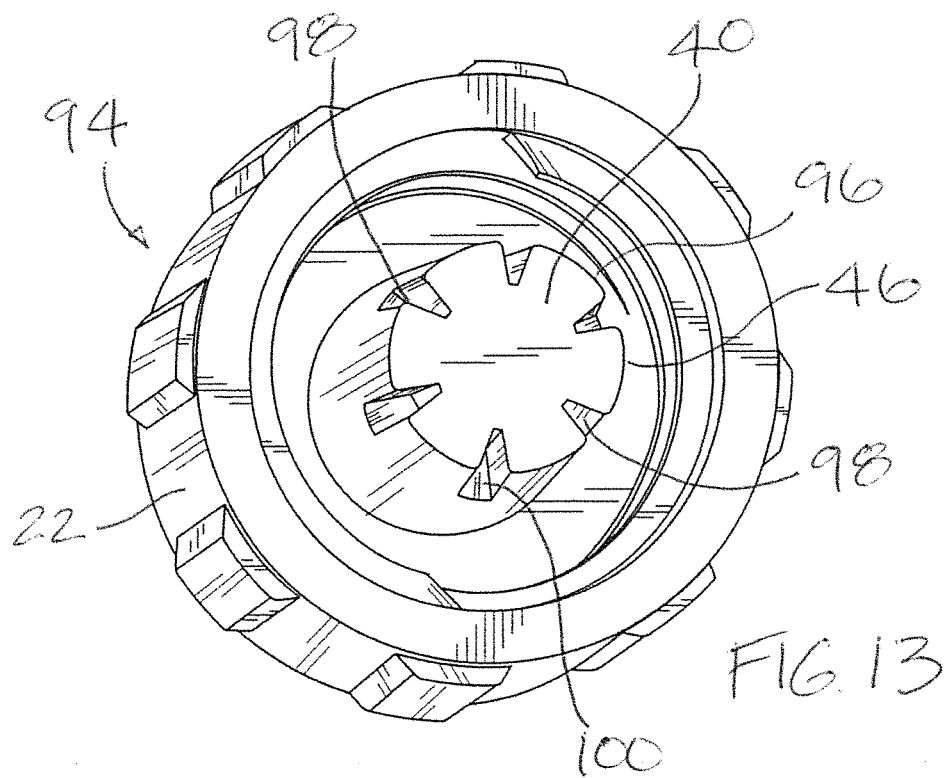
FIG. 13 is a perspective view of still yet another alternative flushing tip adaptor having multiple flow channels.

FIG. 13 is a perspective view of still yet another alternative flushing tip adaptor 94 having a tip 96 with multiple flow channels 98 and a threaded collar 22, which may optionally be omitted. In the present embodiment, the flow channels 98, while including radial cut-outs and axial cut-outs, are formed with narrowing side walls. For example, starting from the bottom wall 100 of each flow channel 98, the side walls narrow or taper inwardly toward one another to the intersection 46. At the intersection 46, the side walls of the radial cut-out taper inwardly in the direction of the central point of the tip end 40. Thus, the present flushing tip adaptor 94 is understood to include a plurality of flow channels 98 each including a first trapezoid cut-out along an axial direction and a second trapezoid cut-out along a radial direction. Wherein the first trapezoid is larger than the second trapezoid. Although six flow channels 98 are shown, fewer or more than six flow channels may be incorporated. Also, a central port 50 may be incorporated. By incorporating the instant flow channels at the tip, the adaptor is configured to produce a wider spray or flow pattern than a single flow stream out a central lumen of a typical prior art syringe.

Figure 14:
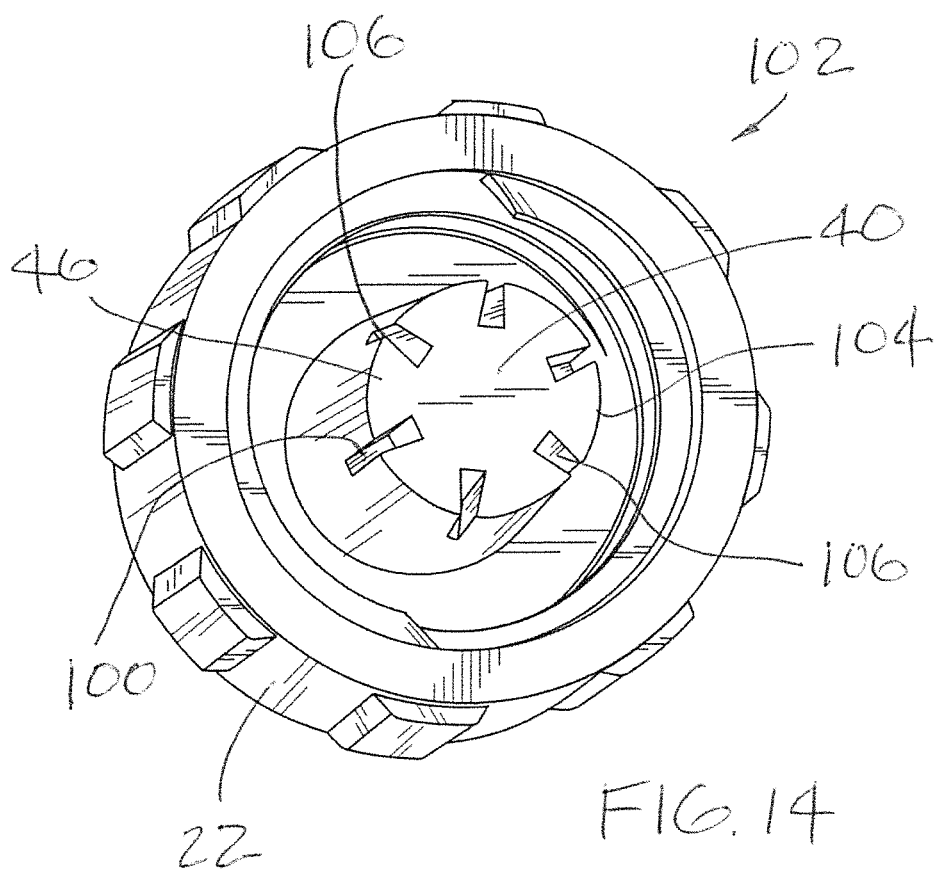
FIG. 14 is a perspective view of still yet another alternative flushing tip adaptor having multiple flow channels.

FIG. 14 is a perspective view of still yet another alternative flushing tip adaptor 102 having a tip 104 with multiple flow channels 106 and a threaded collar 22, which may optionally be omitted. In the present embodiment, the flow channels 106, while including radial cut-outs and axial cut-outs, are formed with enlarging or diverging side walls. For example, starting from the bottom wall 100 of each flow channel 106, the side walls diverge or taper outwardly away one another to the intersection 46. At the intersection 46, the side walls of the radial cut-out taper outwardly in the direction of the central point of the tip end 40. Thus, the present flushing tip adaptor 94 is understood to include a plurality of flow channels 106 each including a first trapezoid cut-out along an axial direction and a second trapezoid cut-out along a radial direction. Wherein the first trapezoid is smaller than the second trapezoid. Although six flow channels 106 are shown, fewer or more than six flow channels may be incorporated. Also, a central port 50 may be incorporated. By incorporating the instant flow channels at the tip, the adaptor is configured to produce a wider spray or flow pattern than a single flow stream out a central lumen of a typical prior art syringe.

FIG. 15 is a cross-sectional side view of an alternative flushing tip adaptor 108 having a tip 110 with multiple flow channels 112 having a rotatable threaded collar 114 provided in accordance with the aspects of the present device, system, and method. The flushing tip adaptor 108 is similar to the flushing tip adaptor 52 of FIGS. 4-7 with the exception of the rotatable collar relative to the tip body 54 and the receiving end 56 is sized to receive a tubing. Such as a device is commonly referred to as an adaptor for a drip line or extension line. However, the receiving end may incorporate a female Luer taper. In the present example, a tapered skirt section 116 and a flange 118 are provided on the exterior surface of the tip body to define a notch 120 therebetween. The collar has a bottom 122 with an opening 124 sized to slide over the tapered skirt section 116 and retained at the notch 120. A curved or arcuate nose section 126 of the opening 124 is provided to facilitate assembly of the collar 114 over the taper skirt section 116. Once installed, the collar is retained within the notch and is rotatable relative to the tip 110 or the body of the tip, which has the plurality of flow channels 112. Although the axial cut-outs 66 appear generally rectangular, the cut out configuration can embody a number of different shapes, such as those discussed above.

FIG. 16 is a side view of the flushing tip adaptor 108 of FIG. 15 shown without the rotatable threaded collar 114. A plurality of spaced-apart gripping members 128 may be incorporated on the exterior surface of the body 130 to facilitate gripping. Although shown as equally spaced apart elongated beams, the gripping members may have other shapes, such as round or semi-spherical projections. In one example, the flushing tip adaptor 108 is practiced without the collar.

To use the alternative flushing tip adaptor 108, the tip 110 is first inserted into a female receiving end of a vascular access device, such as a catheter, and then rotating the collar relative to the body 130 to engage external threads located on the vascular access device. Preferably, a tubing is first attached to the receiving end 56 of the body 130 before connecting the flushing tip adaptor 108 to the vascular access device. If the receiving end 56 is equipped with a female Luer, then the receiving end can be connected to a standard syringe.

Figure 17:
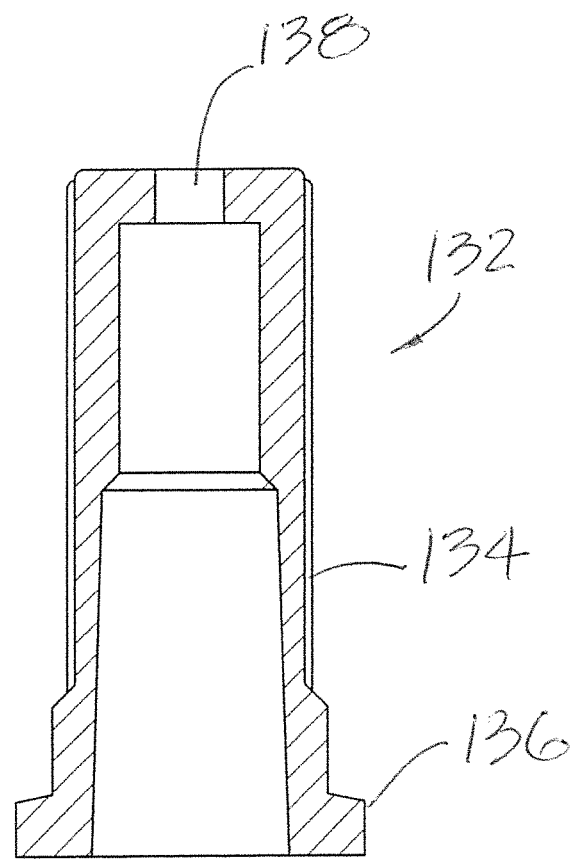
FIG. 17 is a cross-sectional side view of a cap.

FIG. 17 is a cross-sectional side view of a cap 132 provided in accordance with aspect of the present device, system, and method. The cap is shown with a body 134 having a base with threads 136 for threaded engagement with a collar. The cap 132 further comprises a vent opening 138 to permit capping a tip, such as on a syringe or a flushing tip adaptor described elsewhere herein, and avoiding air lock. The cap is sized to receive a luer tip.

Figure 18:
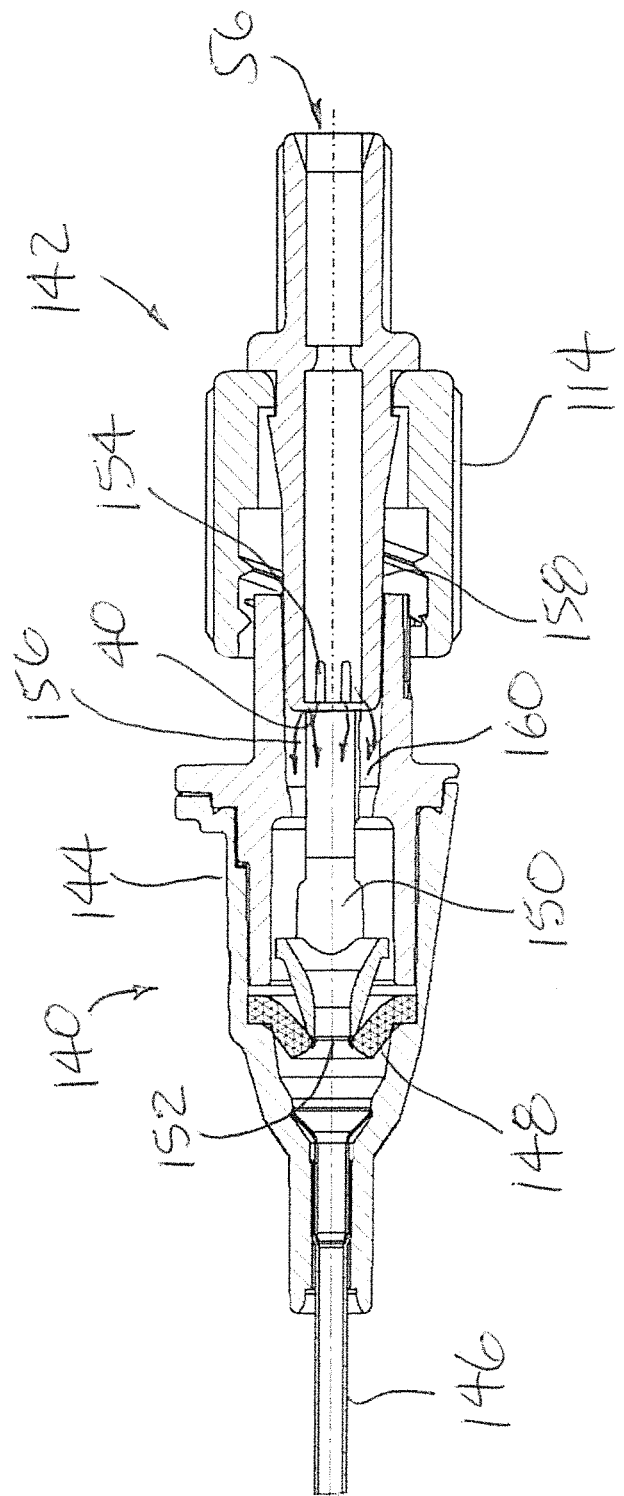
FIG. 18 is a cross-sectional side view of a catheter comprising a valve and a valve actuator and having a flushing tip adaptor engaged at a proximal end for opening the valve and flushing the catheter.

FIG. 18 is a cross-sectional side view of a catheter 140 attached to a flushing tip adaptor 142, which represents the flushing tip adaptor when in normal use, but without a syringe or other fluid source, such as a drip line, typically attached to the receiving end 56 of the flushing tip adaptor. The catheter is shown without a needle, a needle hub, and a needle guard and is therefore representative of a catheter following successful catheterization. Exemplary safety intravenous catheters or IVCs are disclosed in U.S. Pat. Nos. 7,736,339; 7,374,554; 7,625,360; 5,879,337; and 6,629,959 and in publication No. WO 2010/093792 A1, filed Feb. 11, 2010; the contents of each of the foregoing are expressly incorporated herein by reference. The disclosed tip adaptors discussed herein are usable with any of the incorporated catheter assemblies. Alternatively, the syringe of FIGS. 1-3 may be connected directly to the catheter without the tip adaptor.

As shown, the catheter 140 comprises a catheter hub 144, a catheter tube 146, an openable and closeable valve 148, and a valve actuator 150. Similar catheter assemblies are described in U.S. Pat. No. 7,736,339. In a normal closed or sealed state without the flushing tip adaptor engaging the catheter, the valve actuator 150 is pushed to the right of FIG. 18 by the resiliency of the valve 148 and the valve flaps are generally positioned vertically to close the flow opening 152. Upon insertion of the tip adaptor 142, the tip end 40 of the tip abuts the valve actuator 150 and pushes the actuator into the valve 148 to open the valve, as shown in FIG. 18. In the open state as shown, fluid that is discharged through the tip flows through a plurality of flow channels 154 in a large flow pattern 156, indicated by the flow arrows distal of the tip. The large flow pattern 156 allows the interior chamber 160 to be flushed with fluids flowing from the syringe or flushing tip adaptor. As a comparison, a prior art syringe is more likely to produce a flow pattern that is represented by the two interior arrows 156 only since fluid from the prior art syringe would flow from a single central lumen located in the syringe tip. Hence, less or smaller areas of the interior chamber 160 of the catheter hub 144 will be flushed from the smaller flow pattern as compared to the flow pattern generated by the medical flushing device of the present assembly and method. The flow channels 154 can be sized to facilitate flushing of a groove in the side of the female luer, where the legs of the valve opener were previously located before they were pushed forward by the male luer tip. Likewise, the flow channels 154 can be sized narrower than the legs of the valve opener so that the push forward to open the valve is contacts at least part of the tip end.

Figure 19:
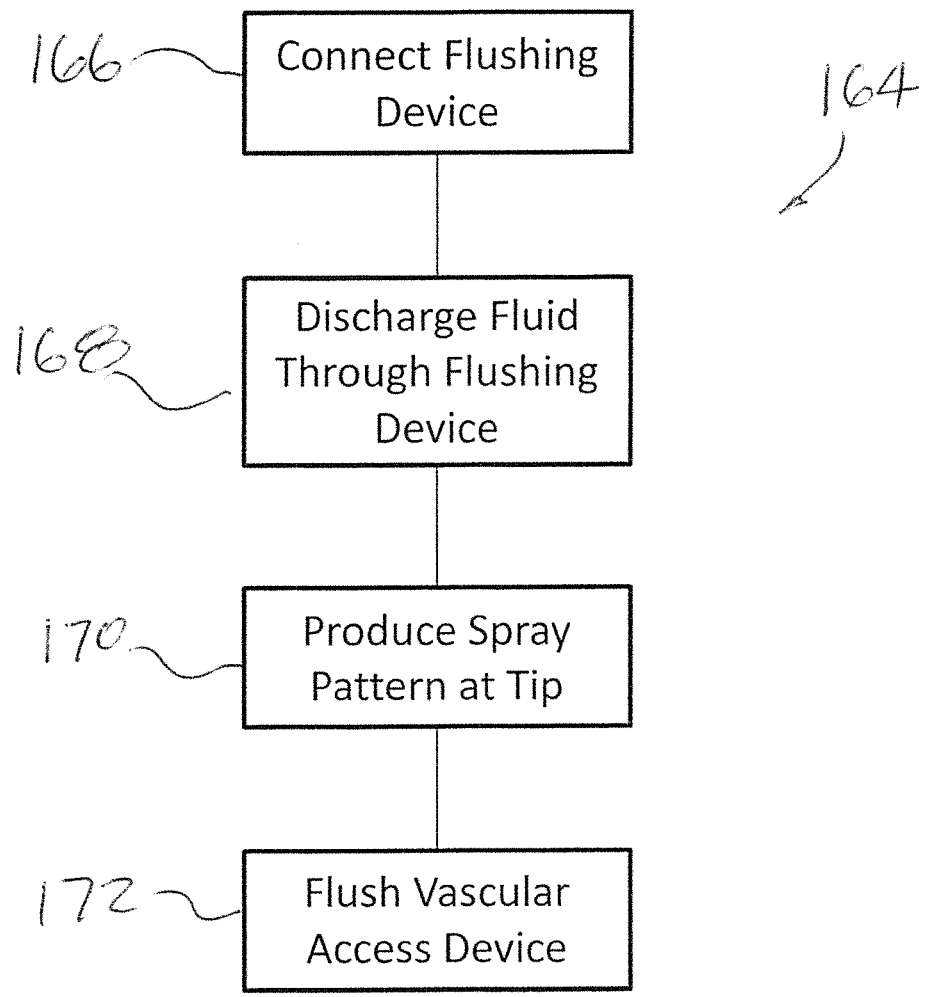
FIG. 19 is a schematic flow diagram showing a method for using a flushing medical device in accordance with aspect of the present method.

FIG. 19 is a schematic flow diagram showing a method 164 for using a flushing medical device in accordance with aspects of the present method. In one example, the method comprises connecting a flushing medical device to a vascular access device at step 166. The method further comprising discharging or allowing fluid through the medical flushing device at step 168. For example, pushing or exerting pressure on a plunger to discharge fluid through a barrel of a syringe to exit through the medical flushing device. Alternatively, allowing fluid to flow by gravity or a pressure differential generated by an automated infusion device. As discussed above, the syringe itself may include a tip having multiple flow channels each comprising a radially located cut-out and an axially located cut-out and itself a flushing medical device. Alternatively, a flushing tip adaptor may be connected to the vascular access device and a prefilled syringe is connected to it. Fluids usable with the present method include Antibiotics (such as Cefuroxime, Ceftriaxone, Meropenem, Imipenem, Amoxicillin, Pip/Com Pip/Tazo, Ciprofloxacin, Levofloxacin, Moxifloxacin, Metronidazol, Vancomycin, and Daptomycin), Antimycotics (such as Fluconazol Amphotericin B, and Caspofungin), Virustatics (such as Gangciclovir and Foscavir), longterm infusion fluid (such as KCL, Propofol, Sufentanil, Insulin, Midazolam, Nimodipin, Heparin, Furosemid, Glutamin, Hydrocortison, Ketamin, Amiodaron, Urapidil, Danaparoid, Milrinon, and Glyceroltrinitrat), Cathecholamine (such as Noradrenalin, Adrenalin, Dopamin, and Dobutamin), and Emergency set (such as Noradrenalin, Adrenalin, Morphin, and Sufentanil).

The method further comprising the step of producing a spray pattern at the tip of the flushing medical device at step 170. The spray pattern is larger than a typical pattern produced by a prior art tip having a single central lumen. As discussed above, the spray pattern can be produced by a plurality of flow channels and an optional central port. The flow pattern can be influenced by the size of each flow channel and the flow channel configuration, such as rectangular, trapezoidal, spiral, etc. The method further comprises the step 172 of flushing the vascular access device with the produced spray pattern. The spray pattern is configured to flush more interior surface area of the vascular access device than for the flow produced from a tip having a single central lumen.

In another embodiment, a syringe having the disclosed tip with multiple flow channels and spray pattern is used to wet bandages. For a single fluid discharge through the tip of the present device, more surface area of a bandage is wet compared to a single fluid discharge out a tip having a single central lumen.

Although limited embodiments of syringe assemblies, flushing tip adaptors, and their components have been specifically described and illustrated herein, many modifications and variations will be apparent to those skilled in the art. Furthermore, it is understood and contemplated that features specifically discussed for one medical flushing device may be adopted for inclusion with another medical flushing device provided the functions are compatible. For example, certain flow channel configuration or shape from one tip adaptor may be combined with another flow channel configuration to have multiple flow configurations on a single flushing tip. Accordingly, it is to be understood that the syringe assemblies, flushing tip adaptors, and their components constructed according to principles of the present device, system, and method may be embodied other than as specifically described herein. The invention is also defined, at least in part, in the following claims.

What is claimed is:

1. A flushing medical device comprising:
a tip having a body comprising a tip end having a generally planar end surface that is generally orthogonal to a side wall having a Luer taper, wherein the tip end and the side wall define an intersection therebetween and wherein the side wall has a greater surface area than a surface area on the tip end;
a lumen formed by the side wall; and
wherein at least one cut-out is formed through the side wall and through the tip end at the intersection and one centrally located port is formed through the generally planar end surface.

2. The flushing medical device of claim 1, wherein the at least one cut-out formed through the intersection has a spiral curve shape.

3. The flushing medical device of claim 1, further comprising a receiving end located opposite the tip end, the receiving end having an interior wall surface with a female Luer taper.

4. The flushing medical device of claim 1, further comprising a tapered skirt and a flange defining a notch on the body.

5. The flushing medical device of claim 1, further comprising a threaded collar.

6. The flushing medical device of claim 4, further comprising a collar that is rotatable relative to the body.

7. The flushing medical device of claim 1, further comprising a syringe barrel attached to the tip and a plunger located inside the syringe barrel.

8. The flushing medical device of claim 1, wherein the tip is formed to a syringe barrel having a plunger located inside the syringe barrel.

9. The flushing medical device of claim 8, wherein the plunger is slidably disposed inside the barrel and comprises a push flange.

10. The flushing medical device of claim 1, further comprising a cap fitted over the tip.

11. The flushing medical device of claim 1, further comprising a catheter hub and the tip is disposed, at least in part, in an interior cavity of the catheter hub.

12. The flushing medical device of claim 1, further comprising a central lumen and a second cut-out formed through the side wall and through the tip end at the intersection.

13. The flushing medical device of claim 1, further comprising a perimeter defining an opening formed only through the surface area of the tip end.

14. The flushing medical device of claim 1, further comprising a second cut-out formed through the side wall and through the tip end at the intersection thereof and spaced apart from the at least one cut-out.

15. A flushing medical device comprising:
a tip having body a comprising a tip end having a generally planar end surface that is generally orthogonal to a side wall having a Luer taper, wherein the generally planar end surface of the tip end and the side wall define an intersection therebetween and wherein the side wall has a greater surface area than a surface area of the generally planar end surface of the tip end;
a lumen formed by the side wall;
a receiving end having a female Luer taper;
a threaded collar located exteriorly of the body; and
wherein at least one cut-out is formed through the side wall and through the tip end at the intersection and one centrally located port is formed through the generally planar end surface.

16. The flushing medical device of claim 15, wherein the at least one cut-out formed through the intersection has a spiral curve shape.

17. The flushing medical device of claim 15, further comprising a second cut-out formed through the side wall and through the tip end at the intersection and spaced apart from the at least one cut-out and the one centrally located port.

18. A flushing medical device comprising:
a tip having a body comprising a tip end having a generally planar end surface that is generally orthogonal to a side wall having a Luer taper, wherein the tip end and the side wall define an intersection therebetween and wherein the side wall has a greater surface area than a surface area of the generally planar end surface of the tip end;
a lumen formed by the side wall;
a barrel attached to the tip;
a plunger slidably disposed inside the barrel; and
wherein at least one cut-out is formed through the side wall and through the tip end at the intersection and one centrally located port is formed through the generally planar end surface.

19. The flushing medical device of claim 18, wherein the tip is unitarily formed with the syringe barrel.

20. The flushing medical device of claim 18, further comprising a second cut-out formed through the side wall and through the tip end at the intersection and spaced apart from the at least one cut-out and the one centrally located port.

21. The flushing medical device of claim 18, further comprising a threaded collar.

* * * * *